United States Patent [19]

Carney et al.

[11] 4,187,372

[45] Feb. 5, 1980

[54] SELDOMYCIN FACTOR 5 DERIVATIVE

[75] Inventors: Ronald E. Carney, Gurnee; James B. McAlpine; Thomas J. Perun, both of Libertyville, all of Ill.

[73] Assignee: Abbott Laboratories, North Chicago, Ill.

[21] Appl. No.: 721,613

[22] Filed: Sep. 8, 1976

[51] Int. Cl.² ............................................. C07H 15/22
[52] U.S. Cl. ................................. 536/17 R; 424/180; 536/10
[58] Field of Search ............................. 536/17, 10

[56] References Cited

U.S. PATENT DOCUMENTS

| 3,781,268 | 12/1973 | Kawaguchi et al. | 536/10 |
| 3,897,412 | 7/1975 | Naito et al. | 536/17 |
| 3,929,761 | 12/1975 | Umezawa et al. | 536/10 |
| 3,939,043 | 2/1976 | Nara et al. | 536/17 |
| 4,078,139 | 3/1978 | Barton et al. | 536/17 |

*Primary Examiner*—Johnnie R. Brown
*Attorney, Agent, or Firm*—Robert L. Niblack; Gildo E. Fato

[57] ABSTRACT

Described are novel derivatives of seldomycin factor 5 (XK-88-5) and particularly 3'-deoxyseldomycin factor 5, which exhibit improved activity against gram-positive and gram-negative bacteria resistant to aminoglycoside antibiotics, and a method of preparing them.

9 Claims, No Drawings

SELDOMYCIN FACTOR 5 DERIVATIVE

BACKGROUND OF THE INVENTION

Seldomycin factor 5 is a pseudotrisaccharide antibiotic elaborated by the microorganism *Streptomyces hofunensis* and for which the formula

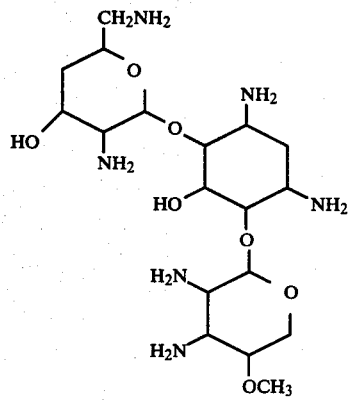

has been elucidated. Seldomycin factor 5 is also identified as XK-88-5. It is a highly active antibiotic, effective against both gram-positive and gram-negative organisms such as *Staphlococcus aureus, Klebsiella pneumoniae, Escherichia coli,* and Proteus, Enterobacter and Salmonella species. Seldomycin factor 5 is only one of a number of antibiotics produced by the fermentation of *Streptomyces hofunensis.* The isolation and characterization of seldomycin factor 5 is described in U.S. Pat. No. 3,939,043, issued Feb. 17, 1976.

The nomenclature of the above and following formulas is simplified by the following numbering system

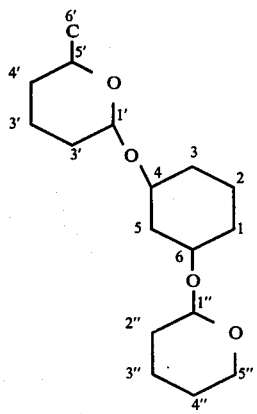

in which the carbons of the cyclitol moiety, also known as the 2-deoxystreptamine moiety, are numbered 1 through 6. The carbons of the hexose moiety are numbered with a single prime, 1' through 6', and the carbons of the pentose moiety are numbered with a double prime, 1" through 5".

Microorganisms are known to frequently acquire resistance to aminoglycoside antibiotics by a mechanism known in the art as "R-Factors". Very generally an R-factor is the extrachromosomal genetic capability of biochemically modifying the antibiotic in such a way as to interfere with its antibacterial action, thereby enabling the organism to grow. Some of the known mechanisms of R-factor mediated resistance involve the attachment of a phosphate ester grouping to the hydroxyl group of kanamycin or neomycin analogous to the hydroxyl group at C3' in seldomycin factor 5. It is known in the art that the replacement of an hydroxyl with a hydrogen will frequently overcome such a mechanism of resistance. It is desirable to obtain compounds which exhibit a broad spectrum of activity against strains of organisms which are resistant to other aminoglycosides.

SUMMARY OF THE INVENTION

Described are seldomycin factor 5 derivatives of the following general formula:

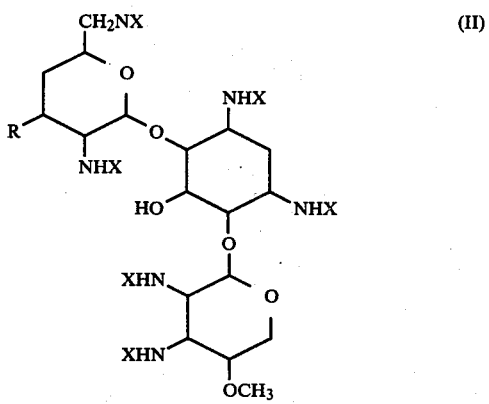

wherein R represents H, OH and

(wherein Y represents lower alkyl, lower aryl, heterocyclic radical or alicyclic radical and wherein X represents an amine protecting group) and the compound of the following formula:

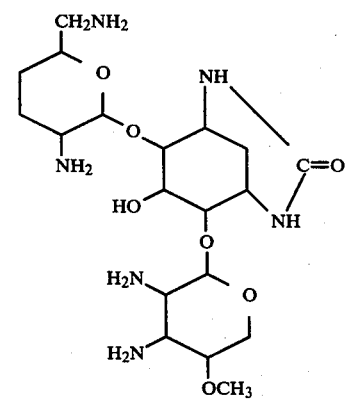

In particular, the invention relates to the derivative 3'-deoxyseldomycin factor 5 which is effective against bacteria known to be resistant to aminoglycoside antibiotics. The compounds of this invention are made as hereinafter described, beginning with seldomycin factor 5, the characteristics and preparation of which are described in U.S. Pat. No. 3,939,043.

DETAILED DESCRIPTION OF THE INVENTION

In summary, this invention relates particularly to a novel derivative of seldomycin factor 5, namely 3'-deoxyseldomycin factor 5, which exhibits improved activity against a wide range of gram-positive and gram-negative bacteria known to be resistant to aminoglycoside antibiotics containing an hydroxyl group in the 3' position and also to bacteria not known to have this mechanism of resistance. The invention further relates to the method for preparing 3'-deoxyseldomycin factor 5 and to intermediates in the preparation thereof. The following process for the removal of the hydroxyl group at C3' in seldomycin factor 5 has been found satisfactory.

The amine groups of seldomycin factor 5 are protected with an "amine-protecting-group". This term is well recognized in the art and includes such groups as substituted and unsubstituted acyl, alkoxycarbonyl, and arylalkoxycarbonyl. The amine-protected seldomycin factor 5 is then converted into a thionoester at the hydroxyl group attached to C3'. It has been found that treatment of an amine-protected seldomycin factor 5 with 1,1'-thiocarbonyldiimidazole in a suitable solvent such as tetrahydrofuran produces the 3'-imidazole-1-thiocarbonyl ester of the amine-protected seldomycin factor 5 with negligible ester formation at the hydroxyl group attached to C5.

Treatment of the 3'-thionester derivative of the amine-protected seldomycin factor 5 with tri-n-butyltin hydride in a suitable solvent such as dioxane replaces the 3' substituent with a hydrogen atom and the product of the reaction is the amine-protected-3'-deoxyseldomycin factor 5. Removal of the amine-protecting groups by procedures well known in the art gives 3'-deoxyseldomycin factor 5.

Where the amine-protecting group is alkoxycarbonyl, it is found that the usual alkaline hydrolysis conditions produce the compound of formula II. 3'-Deoxyseldomycin factor 5 may be obtained from this compound by vigorous alkaline hydrolysis.

This invention is further illustrated by the following examples:

EXAMPLE I

Seldomycin factor 5-per-N-ethoxycarbamate

A mixture of 10.1 g of seldomycin factor 5 and 30 g of sodium carbonate are dissolved in 200 ml of distilled water and the solution is cooled in an ice bath. A mixture of 30 ml of ethylchloroformate and 50 ml of acetone is added dropwise to this solution and the resulting mixture is allowed to stand at room temperature for two hours. The precipitated product is removed by filtration, washed twice with 200 ml portions of water and dried in vacuo to yield 16.8 g of seldomycin factor 5 per-N-ethoxycarbamate.

Microanalysis: C, 48.98; H, 7.12; N, 9.48%.
Calc. for $C_{36}H_{62}N_6O_{19}$: C, 48.97; H, 7.08; N, 9.52%.

EXAMPLE II

Seldomycin factor 5-per-N-ethoxycarbamate-3'-thioimidazolide

A solution of 15 g of seldomycin factor 5-per-N-ethoxycarbamate in 250 ml of anhydrous pyridine is diluted with 500 ml of tetrahydrofuran and treated with 6 g of 1,1'-thiocarbonyldiimidazole. The reaction mixture is heated under reflux and after four hours a further 4 g of 1,1'-thiocarbonylidiimidazole is added. The reaction mixture is heated under reflux for a further 16 hours and solvent is removed. Chromatography of the residue on a column of silica gel affords 16.4 g of seldomycin factor 5-per-N-ethoxycarbamate-3'-thioimidazolide.

Microanalysis: C, 48.34; H, 6.63, N, 11.11; S, 3.17%.
Calc. for $C_{40}H_{64}N_8O_{19}S$: C, 48.38; H, 6.50; N, 11.29; S, 3.22%

EXAMPLE III

3'-Deoxyseldomycin factor 5-per-N-ethoxycarbamate

A solution of 12.5 g of seldomycin factor 5 per-N-ethoxycarbamate-3'-thioimidazolide in 750 ml of dioxane is added dropwise to a solution of 12.7 ml of tri-n-butylstannane in 1200 ml of dioxane. The mixture is heated under reflux in an atmosphere of nitrogen for two and a half hours and then solvent is removed. Chromatography of the residue over a column of silica gel affords 9.8 g of 3'-deoxyseldomycin factor 5 per-N-ethoxycarbonyl derivative.

Microanalysis: C, 49.60; H, 7.30; N, 9.45%.
Calc. for $C_{36}H_{62}N_6O_{18}$: C, 49.88; H, 7.21; N, 9.69%.

EXAMPLE IV

3'-Deoxyseldomycin factor 5-1N, 3N-ureide

A solution of 4.7 g of 3'-deoxyseldomycin factor 5-per-N-ethoxycarbamate in 450 ml of 1.9 N methanolic sodium hydroxide is heated under reflux overnight. The mixture is adjusted to pH 7 with 10 N sulfuric acid and solvent is removed. The residue is extracted with a mixture of chloroform (4 parts), methanol (6 parts), and concentrated ammonium hydroxide (1 part by volume) and the extract is chromatographed over a column of silica gel to give 2.2 g of 3'-deoxyseldomycin factor 5-1N, 3N-ureide.

EXAMPLE V

3'-Deoxyseldomycin factor 5

Either 4.7 g of 3'-deoxyseldomycin factor 5 per-N-ethoxycarbamate or 2.42 g or 3'-deoxyseldomycin factor 5-1N, 3N-ureide in 50 ml of methanol is added to 50 ml of 12 N aqueous potassium hydroxide solution and the mixture is heated in a sealed tube at 135° C. for 16 hours. The reaction mixture is adjusted to pH 7 with 10 N sulfuric acid and solvent is removed. The residue is extracted with a mixture of chloroform (4 parts), methanol (6 parts), and concentrated ammonium hydroxide (1 part by volume). The extract is chromatographed on a column of silica gel to give 2.3 g of 3'-deoxyseldomycin factor 5.

The sulfate salt of 3'-deoxyseldomycin factor 5 is prepared by treating a methanolic solution of the base with concentrated sulfuric acid. The solid precipitate is filtered off, washed well with methanol, and dried.

Microanalysis: C, 27.09; H, 6.23; N, 10.34%.
Calc. for $C_{18}H_{38}N_6O_6.3\ H_2SO_4.4\ H_2O$: C, 26.99; H, 6.54, N, 10.49%.

These compounds are further characterized by their carbon magnetic resonance spectra, which are listed according to their probable assignments as follows:

Table I*

| Carbon No. | Compound | | | | |
|---|---|---|---|---|---|
| | Example I | Example II | Example III | Example IV | Example V |
| $C_1'$ | 99.6 | 99.5 | 98.2 | 101.2 | 102.2 |

Table I*-continued

| Carbon No. | Compound | | | | |
|---|---|---|---|---|---|
| | Example I | Example II | Example III | Example IV | Example V |
| $C_2'$ | 57.6 | 54.2 | 50.6 | 50.4 | 50.8 |
| $C_3'$ | 64.5 | 80.1 | 23.6 | 27.6 | 27.0 |
| $C_4'$ | 37.0 | 31.9 | 27.3 | 28.4 | 28.4 |
| $C_5'$ | 66.7 | 65.9 | 66.6 | 70.7 | 71.6 |
| $C_6'$ | 44.4 | 43.8 | 44.5 | 45.9 | 45.9 |
| $C_1$ | 50.6 | 50.4 | 50.6 | 47.9 | 51.2 |
| $C_2$ | 34.9 | 34.9 | 34.9 | 18.2 | 36.7 |
| $C_3$ | 49.9 | 49.7 | 49.7 | 45.9 | 50.3 |
| $C_4$ | 82.4 | 82.7 | 82.1 | 77.5 | 88.2 |
| $C_5$ | 74.7 | 74.3 | 74.8 | 71.8 | 75.2 |
| $C_6$ | 79.6 | 79.5 | 79.6 | 80.2 | 87.2 |
| $C_1''$ | 96.9 | 96.6 | 96.8 | 99.0 | 100.2 |
| $C_2''$ | 54.4 | 54.2 | 54.4 | 55.5 | 56.3 |
| $C_3''$ | 53.1 | 53.1 | 53.1 | 55.5 | 54.9 |
| $C_4''$ | 76.3 | 76.2 | 76.2 | 79.3 | 80.3 |
| $C_5''$ | 59.5 | 59.5 | 59.5 | 60.6 | 60.9 |
| $OCH_3$ | 57.6 | 57.4 | 57.5 | 58.6 | 58.8 |

*Only peaks assigned to ψ-trisaccharide carbons are shown. The spectra are described as parts per million (ppm) downfield from tetramethylsilane. Dimethylsulfoxide was used as a solvent for the compounds of Examples I, II, and III and deuterium oxide was used as the solvent for the compounds of Examples IV and V.

3'-deoxyseldomycin factor 5 was tested for antimicrobial activity against gram-positive and gram-negative bacteria in an agar dilution test. Results are given in MIC values (minimum inhibitory concentrations) expressed in micrograms/ml as follows:

Table 2

| Organism | Strain | Seldomycin Factor 5 | 3'-Deoxyseldomycin Factor 5 |
|---|---|---|---|
| Escherichia coli | $R_3$ | >10 | 2.5 |
| Escherichia coli | ATCC 26 | 0.04 | <0.01 |
| Escherichia coli | $R_{18}$ | 1.4 | <0.01 |
| Streptococcus faecalis | 10541 | >10 | 25 |
| Pseudomonas aeruginosa | BMH No. 10 | 10 | 1.25 |
| Pseudomonas aeruginosa | KY 8512 | 14.1 | 1.56 |
| Staphylococcus aureus | ATCC 6438 P | 0.08 | 0.02 |
| Bacillus subtilis | No. 10707 (U. of Ill.) | 0.08 | <0.005 |
| Proteus vulgaris | ATCC 6897 | 0.62 | 0.31 |
| Shigella sonnei | ATCC 9290 | 0.31 | 0.16 |
| Salmonella typhi | ATCC 9992 | 0.31 | 0.08 |
| Serratia marcescens | ATCC 4003 | 0.18 | 0.04 |
| Klebsiella pneumoniae | 10031 | 0.08 | 0.02 |
| Klebsiella pneumoniae | Y-58 | 1.41 | 0.08 |

What is claimed is:

1. A compound of the formula:

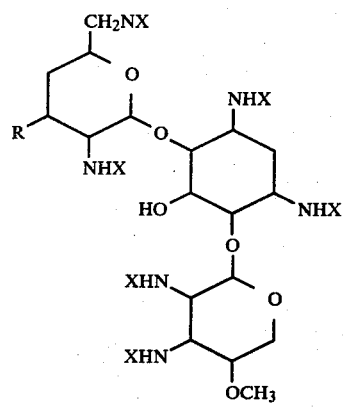

wherein R is a member of the group consisting of H, and

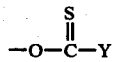

wherein Y is a member of the group consisting of lower alkyl, lower aryl, imidazolyl and wherein X is an amine protecting group and the pharmaceutically acceptable salts thereof.

2. A compound selected from the group consisting of seldomycin 5-per-N-ethoxycarbamate-3'-thiocarboxylimidazolide, 3'-deoxyseldomycin factor 5-per-N-ethoxycarbamate, 3'-deoxyseldomycin factor 5-1N, 3N-ureide and 3'-deoxyseldomycin factor 5.

3. The compound of claim 2: 3'-deoxyseldomycin factor 5-per-N-ethoxycarbamate.

4. The compound of claim 2: 3'-deoxyseldomycin factor 5.

5. The compound of claim 2: seldomycin factor 5-per-N-ethoxycarbamate-3'-thioimidazolide.

6. The compound of claim 2: 3'-deoxyseldomycin factor 5-1N, 3N-ureide.

7. A compound of claim 1 wherein X is selected from the group consisting of unsubstituted acyl, alkoxycarbonyl, and arylaloxycarbonyl.

8. A compound of claim 7 wherein X is carboethoxy.

9. A compound of claim 1 wherein Y is 1-thiocarbonylimidazole.

* * * * *

UNITED STATES PATENT AND TRADEMARK OFFICE
CERTIFICATE OF CORRECTION

PATENT NO. : 4,187,372
DATED : February 5, 1980
INVENTOR(S) : Ronald E. Carney, et. al.

It is certified that error appears in the above—identified patent and that said Letters Patent is hereby corrected as shown below:

In column 6, line 39, "3'-thioimidazolide." should read "3'-thiocarbonylimidazolide.".

In column 6, line 44, "arylaloxycarbonyl" should read "arylalkoxycarbonyl".

Signed and Sealed this

Twenty-eighth Day of April 1981

[SEAL]

Attest:

RENE D. TEGTMEYER

Attesting Officer

Acting Commissioner of Patents and Trademarks